United States Patent [19]

Hawk

[11] 4,286,950

[45] Sep. 1, 1981

[54] COVER FOR DENTAL HANDPIECE BUR

[76] Inventor: Gene R. Hawk, 139 Fair Ave., NE., New Philadelphia, Ohio 44663

[21] Appl. No.: 133,012

[22] Filed: Mar. 24, 1980

[51] Int. Cl.³ .................................................. A61C 1/16
[52] U.S. Cl. .................................................. 433/116
[58] Field of Search .................................................. 433/116

[56] References Cited

U.S. PATENT DOCUMENTS

| | | | |
|---|---|---|---|
| 886,862 | 5/1908 | Repsold | 433/116 |
| 1,834,726 | 12/1931 | Ozon | 433/116 |
| 2,073,137 | 3/1937 | Bimrose | 433/116 |

*Primary Examiner*—Robert Peshock
*Attorney, Agent, or Firm*—Oldham, Oldham, Hudak & Weber Co.

[57] ABSTRACT

A cover for a dental handpiece end and a bur positioned thereon, the cover forms a resilient boot-like structure of generally L-shape having an enlarged leg portion with an open end adapted to engage the end of a dental handpiece and an open ended foot portion adapted to encompass a dental drill or bur on the handpiece end, the boot is split on a line extending from the foot portion open end to the enlarged leg open end on its inner surface to facilitate engagement with the handpiece.

4 Claims, 5 Drawing Figures

COVER FOR DENTAL HANDPIECE BUR

BACKGROUND OF THE INVENTION

Heretofore there have been various types of sanitary covers provided for a dental handpiece, such as the tubular structure shown in U.S. Pat. No. 2,073,137, while a protector for a dental drill piece has also been provided and is shown in U.S. Pat. No. 2,041,077. These types of shields or protectors also are represented by a sack-like shield for dental instruments, as shown in the relatively tubular structure, to engage a dental handpiece, as indicated in U.S. Pat. No. 1,093,865.

However, one problem that none of such prior types of shields have solved is that relating to the fact that the dental bur is a relatively sharp abrasive intrument or tool. This tool, if it is positioned around a dentist chair, can cause problems if the dentist accidentally strikes this grinding bur and abrades or cuts his arm or hand, or the dental assistant may be cut or scratched by the bur.

It is the general object of the present invention to provide a new and improved cap-type cover for a dental handpiece, and especially to provide a removable cover for the abrasive grinding bur or tool mounted in a dental handpiece.

Another object of the invention is to provide a cover that can be readily engaged with, and disengaged from, a dental handpiece for covering the grinding tool positioned therein to prevent accidental contact by one working near the dental chair with such a grinding bur or handpiece.

Another object of the invention is to provide a plastic, relatively stiff cap-type cover for a dental handpiece bur or drill to render such tool inactive and safe, and to protect the tool and enclose it when not in use.

The foregoing and other objects and advantages of the invention will be made more apparent as the specification proceeds.

In the accompanying drawings.

When referring to corresponding members shown in the drawings and referred to in this specification, corresponding numerals are used to facilitate comparisons therebetween.

SUBJECT MATTER OF THE INVENTION

A cover for a dental handpiece bur or drill comprising a resilient boot-like structure of generally L-shape and having an enlarged leg portion with an open end adapted to engage the end of the dental handpiece and an open-ended foot portion adapted to encompass a dental bur carried by the handpiece, the said structure being slotted on a line extending from the foot portion open end to the enlarged leg end on the inner surface of the L-shaped structure.

Figure 1:
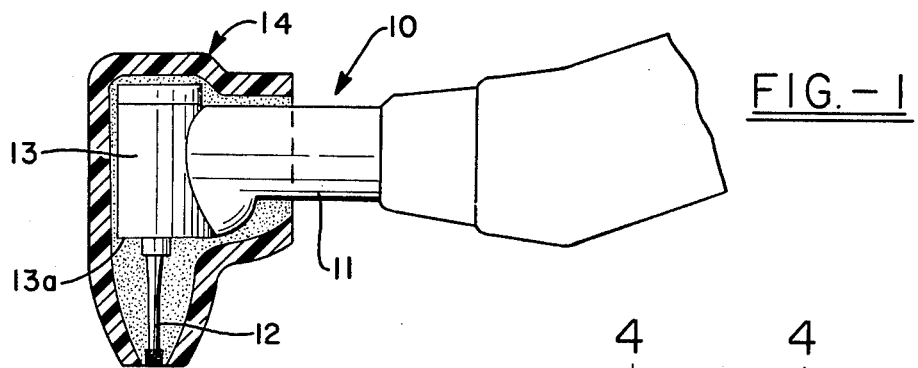
FIG. 1 is a fragmentary side elevation of the dental handpiece with a cover of the invention enclosing an end portion of the handpiece and a bur thereon and being partially shown in vertical section.
Figures 2, 3:
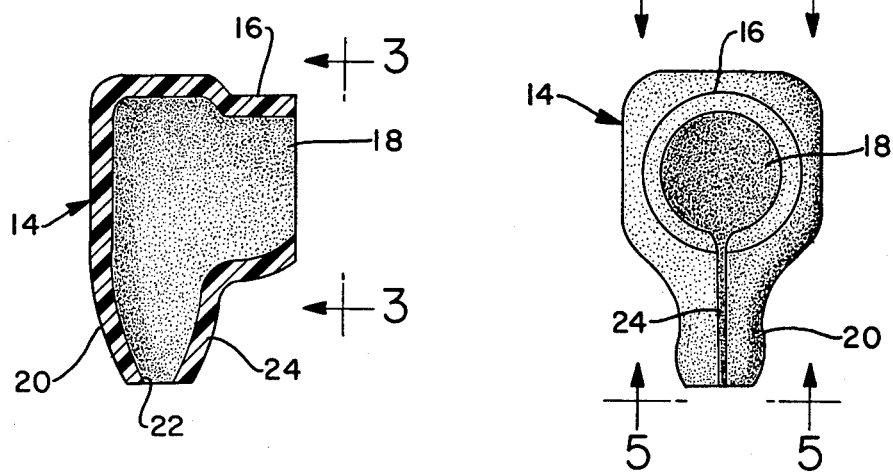
FIG. 2 is a vertical section of the cover of the invention.
FIG. 3 is an elevation of the cover of FIG. 2 taken on line 3—3 thereof.
Figure 4:
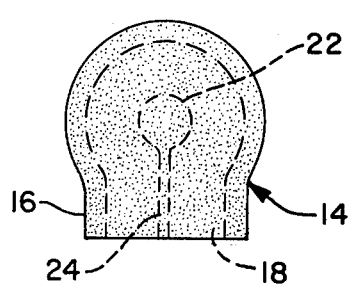
FIG. 4 is an elevation of the cover of FIG. 3 taken on line 4—4 thereof.
Figure 5:
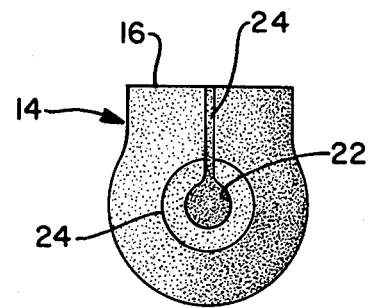
FIG. 5 is a bottom elevation of the cover of FIG. 3 taken on line 5—5 thereof.

Attention now is particularly directed to the details of the structures shown in the accompanying drawings, and an end portion of the dentist's handpiece as indicated by the numeral 10 and this handpiece is of the type that normally positions a bur or drill 12 in an end of the handpiece with such a bur extending from the handpiece in the manner shown in the drawings. The bur has a sharp drilling or contoured abrading end, and frequently a dentist or his assistant may brush against this exposed bur on the handpiece and be scratched or cut. So as to avoid any such injury to the dentist or his assistant, the present invention provides a cover 14 for this handpiece and bur. The cover 12 is normally made from a translucent, resilient plastic material, such as vinyl, and it is thick enough for sufficient strength and size so that it can be snapped or pressed over into engagement with the end of the dental handpiece, and to be pried or pulled from engagement with the end of the handpiece. The handpiece 10 has a reduced diameter neck 11 adjacent an enlarged end portion 13 including an offset foot section 13a. Thus section 13a rotatively mounts the driven bur 12 to extend from the hand piece at about a 90 degree angle relationship to the longitudinal axis of the handpiece. As best shown in FIG. 2 of the drawings this cover 14 is of generally L-shape in section and it is a boot-like structure with an enlarged base leg portion 16 having an open end 18. This structure also includes a foot portion 20 having an open end 22. The foot portion is of generally conical shape and it reduces in diameter as it approaches its open end 22. Normally, both the base leg and foot portions are of generally circular shape in section and the boot-like structure is largest in area where the base leg connects to the foot portion.

So as to facilitate snapping or bringing the cover into engagement with the dental handpiece, a slot 24 is formed in the cover 14 and it extends from the open end 18 of the base leg to the open end 22 of the foot portion on the inner surface of the cover. The cover 14 is sized complementary to the end portion of the handpiece and is resilient and flexible to adapt and engage handpiece end portions of various shapes and sizes, all of which are generally the same as the handpiece shown.

It will be noted that the cover is of such size as to have a portion that would be in resilient engagement with the neck portion 11 of the handpiece and then the cover enlarges slightly to engage the drill end. Naturally the foot portion 20 of the cover is long enough to extend up to the end of the bur or drill and/or to extend slightly therebeyond, if desired. Normally the foot portion is of sufficient diameter as to loosely receive or enclose the bur 12 therein.

The cover of the invention can be made from any suitable material of suitable strength and thickness. It is durable and attractive so as to not be objectionable to the dentist or his patients. The handpiece cover 14 is capable of being washed or cleaned in a conventional manner.

The cover is resilient and durable and can be used for reasonable length of time to protect the dental drill and avoid accidental cutting of persons coming into working association with this dental handpiece. Hence, it is believed that the object of the invention has been achieved.

While one complete embodiment of the invention has been disclosed herein, it will be appreciated that modification of this particular embodiment of the invention may be resorted to without departing from the scope of the invention.

What is claimed is:

1. A cover for a dental handpiece end and a bur or other tool positioned thereon, which bur extends substantially at a right angle to the longitudinal axis of the handpiece, comprising a tubular boot-like structure of generally L-shape, having an enlarged leg portion with an open end adapted to engage the end of a dental handpiece and an open ended smaller diameter foot portion adapted to encompass the handpiece end and a dental drill or bur positioned thereon, said structure being split on a line extending continuously from the foot portion open end to the enlarged leg open end on the inner surface of the L-shaped structure said structure having some resilience and flexibility to enable it to be sprung into and out of engagement with the handpiece end and tool thereon.

2. A cover for a dental handpiece bur as in claim 1, where said foot portion is of roughly conical shape and tapers inwardly towards its open end to encompass but be spaced from the bur.

3. A cover for a dental handpiece bur as in claim 1, where said leg portion open end is of circular shape and is of smaller diameter than a portion of the cover connecting said leg portion and said foot portion to aid in retaining the cover in engagement with the handpiece end.

4. A cover for a dental handpiece bur as in claims 1 or 2, where said split comprises a straight line slot in the wall of the boot-like structure extending completely from the open end of said leg to the open end of said foot portion.

* * * * *